(12) United States Patent
Hammock et al.

(10) Patent No.: US 6,528,675 B1
(45) Date of Patent: Mar. 4, 2003

(54) CYANOHYDRIN ETHERS AND ESTERS AS HIGH-SENSITIVITY ENZYME SUBSTRATES

(75) Inventors: Bruce D. Hammock, Davis, CA (US); Guomin Shan, Davis, CA (US); Rong Zhang, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/971,105

(22) Filed: Oct. 3, 2001

(51) Int. Cl.$^7$ .......................................... C07C 255/03
(52) U.S. Cl. ...................... 558/407; 558/406
(58) Field of Search ................. 558/407, 406

(56) References Cited

PUBLICATIONS

Shane, Guomin et al., Development of Sensitive Esterase Assays Based on .alpha.–Cyano–Containing Esters. Analytical Biochemistry (2001), 299 (I), 54–62.*

Bilban, M. et al., "New fluorogenic substrate for the first continuous steroid sulfatase assay." Bioorg Med Chem Lett; 10(9):967–969 (May 1, 2000) Abstract.

Cheviron, N., et al., "Coumarin–Ser–Asp–Lys–Pro–OH, a fluorescent substrate for determination angiotensin–converting enzyme activity via high–performance liquid chromatography." Anal. Biochem, 280(1):58–64 (Apr. 10, 2000) Abstract.

Corey, E. et al., "Enantioselective Conversion of Aldehydes to Cyanohydrins by a Catalytic System with Separate Chiral Binding Sites for Aldehyde and Cyanide Components." Tetrahedron Letters, vol. 34, No. 25, pp. 4001–4004, (1993) Great Britain.

Effenberger, F., "Synthesis and Reactions of Optically Active Cyanohydrins." Angew. Chem. Int. Ed. Engl. vol. 33, pp. 1555–1564, (1994).

Ege. S., Organic Chemistry, (1994), pp. 466–477, D.C. Heath and Company Lexington, MA/Toronto.

Gassman, P. et al., "Cyanohydrins—A General Synthesis" Tetrahedron Letters No. 40, pp. 3773–3776, Pergamon Press Ltd. (1978) Great Britain.

Gröger, H., et al., "Asymmetric Synthesis of an (R)–Cyanohydrin Using Enzymes Entrapped in Lens–Shaped Gels" Organic Letters vol. 3, No. 13 pp. 1969–1972 (2001).

Kanai, M. et al., "Design of a new bifunctional asymmetric actalyst from carbohydrates: application to catalytic asymmetric cyanosilylation of aldehydes and acetophenone." Tetrahedron letters vol. 41, pp. 2405–2409 (2000).

Ninkovic, M., et al., "Fluorogenic assay for penicillin G acylase activity." Anal Biochem, 292(2):228–233 (May 15, 2001) Abstract.

* cited by examiner

Primary Examiner—Cecilia Tsang
Assistant Examiner—Ebenezer Sackey
(74) Attorney, Agent, or Firm—Townsend and Townsend and Crew, LLP (57) ABSTRACT

Ethers and esters of cyanohydrins that contain optically detectable moieties are highly effective for detecting, monitoring, and measuring the activity of enzymes that cause the cleavage of certain types of substrates. The cyanohydrins function as proaldehydes and proketones, spontaneously converting to aldehydes and ketones, respectively, which provide a large increase in optical detectability relative to both the starting esters and ethers and the cyanohydrins.

20 Claims, 1 Drawing Sheet

Fig. 1

CYANOHYDRIN ETHERS AND ESTERS AS HIGH-SENSITIVITY ENZYME SUBSTRATES

STATEMENT AS TO RIGHTS TO INVENTIONS MADE UNDER FEDERALLY SPONSORED RESEARCH OR DEVELOPMENT

This invention was made at least in part with Government funding under Contract No. ES02710 awarded by the National Institute of Environmental Health Services, and Contract No. ES04699 awarded by the National Institute of Environmental Health Services Superfund Program. The Government has certain rights to this invention.

BACKGROUND OF THE INVENTION

1. Field of the Invention

This invention resides in the fields of enzymatic reactions and assays for monitoring or detecting enzyme activity. In particular, this invention relates to reporter species that serve as indicators of enzyme activity.

2. Description of the Prior Art

The study and detection of enzyme activity serve a wide range of purposes both in research laboratories and in clinical assays. Enzyme activity is monitored, for example, in monitoring physiological functions in patients during routine checkups or diagnostic procedures in general, in monitoring the exposure of workers and residents to potentially harmful chemicals such as toxic or carcinogenic pesticides or inorganic materials in the atmosphere, soil, or drinking water, in determining the effectiveness of pharmaceuticals on disease states or conditions, in screening new compounds for biological activity as either promoters or inhibitors of particular enzymes, in monitoring gene and transgene expression, and in performing immunological and other laboratory assays such as enzyme-linked immunosorbent assays (ELISAs) and Western blots.

Optical methods of detection, such as fluorescence emission, UV absorptivity, and colorimetry are convenient and highly effective for detecting, monitoring, and measuring enzyme activity, since methods such as these can generate either qualitative or quantitative information and detection can be achieved either by direct visual observation or by instrumentation. Optically detectable reporters, i.e., synthetic or substitute substrates that are added to a sample and that display a measurable increase or other difference in optical detectability upon action of the enzyme, are therefore particularly useful. Examples of optical reporters that are currently known are 4-nitrophenol, $\alpha$-naphthol, $\beta$-naphthol, resorufin and substituted resorufins, nitranilide, ethanol, 5-bromo-4-chloro-3-indole, and umbelliferone derivatives. The degree of change and hence the effectiveness of optical detection reporters depend on any of several factors, depending on the detection method for which they are used. Some of these factors are a high extinction coefficient for reporters that are detectable by light absorptivity (particularly a large increase from substrate to product), a large change in the wavelength at which maximum absorptivity occurs (particularly a large substrate-to-product red shift), a substrate-to-product increase in the Stokes' shift for fluorescent reporters, and the chemical stability of the reporter.

SUMMARY OF THE INVENTION

It has now been discovered that ethers and esters of cyanohydrins are highly effective optical detection reporters for certain types of enzyme activity, notably those that convert the ethers or esters to the cyanohydrins. The cyanohydrins function as proaldehydes and proketones, spontaneously converting to aldehydes and ketones, respectively, under appropriate pH conditions in the neutral to basic range. The use of these cyanohydrin ethers and esters as optical detection reporters derives in each case from a group bonded to the central carbon of the cyanohydrin moiety, the group imparting to the final aldehyde or ketone the optical detectability that serves as the means for detecting the enzyme activity. The effectiveness of these cyanohydrin ethers and esters as reporters derives from large differences in optical properties between the aldehydes and ketones and either the cyanohydrins or the cyanohydrin ethers or esters (i.e., the unconverted reporters). These differences include a larger Stokes' shift (which in fluorescent reporters is the difference between the maximum excitation wavelength and the maximum emission wavelength) of the product (aldehyde or ketone) relative to the substrate (cyanohydrin ether or ester), a larger-substrate-to-product red shift (the difference in maximum absorbance in UV and calorimetric assays and the difference in emission maximum in fluorescence assays), a larger quantum yield (in fluorescence assays the proportion of energy absorbed that is then emitted as light), and a greater extinction coefficient at the maximum wavelength. These differences provide increases in sensitivity and decreases in background relative to prior art reporters, permitting the use of a wider band width, simpler and less costly optics, and various other benefits to the assay as a whole.

This invention resides in novel cyanohydrin esters and ethers as well as novel methods for detection of enzyme activity involving the use of cyanohydrin esters and ethers, both novel and already known, as reporter substances. The many applications and methods of implementation of these substances will be better understood from the description that follows, and further applications and uses will be readily apparent to those skilled in the art.

DETAILED DESCRIPTION OF THE INVENTION AND PREFERRED EMBODIMENTS

Definitions

The term "alkyl" is used herein to refer to a branched or unbranched, saturated or unsaturated, monovalent hydrocarbon radical. While the term "alkyl" is not limited to any particular number of carbon atoms, the most typical alkyl groups will be those having from 1 to 30 carbon atoms, and subranges of interest within this range are 1 to 20, 1 to 12 carbon atoms, 1 to 6 carbon atoms, and 1 to 3 carbon atoms, preferences for particular subranges varying with the location of the alkyl group on the structure. Although the term "alkyl" is defined herein to include unsaturated groups such as olefinic groups and acetylenic groups. and branched groups such as those bearing the prefixes sec, tent, iso, and neo, preferred alkyls are saturated and unbranched. Alkyl groups having from 1 to 6 carbon atoms are referred to as "lower alkyl." Examples of branched alkyls are secondary and tertiary alkyls, such as those of isopropyl, t-butyl, isobutyl, 2-ethylpropyl, etc.

The term "aralkyl" is used herein to refer to an alkyl group substituted with either an aromatic ring (i.e., a phenyl group), two or more fused aromatic rings, or two or more aromatic rings that are linked covalently to one another through one or more single covalent bonds, through a linking alkyl group such as a methylene or ethylene moiety, or through a carbonyl such as that linking the phenyl rings in benzophenone. Examples of fused aromatic rings are naphthyl, anthryl, and phenanthryl. Preferably, the aromatic portion of the aralkyl group is either a phenyl group or up to three fused rings. The alkyl group that is substituted by the aromatic group is as defined in the preceding paragraph. Simple examples of aralkyl groups are benzyl and phenylethyl.

The term "alkoxy" is used herein to refer to an alkyl group as defined above joined to the remainder of the molecule through an ether (—O—) linkage. Common alkoxy groups are methoxy, ethoxy, propoxy, isopropoxy, butoxy, and t-butoxy. Other examples with greater numbers of carbon atoms will be readily apparent to the experienced chemist.

The term "oxiranyl" is used herein to refer to the following group (also known as an epoxide group) in which either of the two carbon atoms serves as the point of attachment to the remainder of the molecule. The terms "oxiranylalkyl," "oxiranylalkoxy," "oxiranylamino" and the like refer to alkyl, alkoxy, and amino groups in which one hydrogen atom is replaced by an oxiranyl group.

The term "peptidylamino" is used herein to refer to polypeptide groups that terminate in an amino moiety, i.e., an —$NH_2$ group one hydrogen of which is replaced by a polypeptide chain. The term "polypeptide" is used herein to denote groups that may be more conventionally known as "oligopeptides" as well as those that may be more conventionally known as "polypeptides." Polypeptide groups thus contain a minimum of two amino acids, and preferably from 2 to 100, more preferably from 3 to 50, and most preferably from 4 to 20, in all cases each pair of adjacent amino acids joined by a peptide bond.

The term "polymethenyl" is used herein to refer to oligomers and polymers in which the repeating unit is shown within the parentheses in the following structure For convenience, the "poly" portion of this term is used herein generically to include the more conventional usages of both "oligo" and "poly." Polymethenyl groups generally form part of the optically detectable label portion of the substrates of this invention, and the number of repeating units, indicated by the index "n" in the above structure, is not critical to the invention and will depend on which particular label is desired. In most cases, however, the number of repeating units will range from 3 to 30, preferably from 3 to 10. An example of a substituted polymethenyl aldehyde is trans-retinal, whose molecular formula is shown below.

The term "mimic" where used herein to describe a first group relative to a second group indicates that the first group bears sufficient steric and electronic similarity to the second group that a particular enzyme activity on the second group will also occur on the first group. Mimics thus bear slight structural variations over their target groups, often by the substitution of one atom for another with at most a small change in the three-dimensional conformation of the group or of the molecule as a whole in the vicinity of the group.

The definitions of the various "R" groups in this specification and the appended claims include the word "substituted" to refer to particular subclasses of groups within the definitions. The word "substituted" denotes that one or more of the hydrogen atoms of the group that is substituted is replaced with a monovalent group other than hydrogen. The variety of possible substituents will be well known and readily apparent to the typical synthesis chemist, and for those substituents that are not located at the site of attack of the enzyme, the identity of the substituent has little or no bearing on the ability of the compounds to serve as an enzyme substrate for any of the various substrate functions described in this specification. Substituents that are located close to the site of attack of the enzyme, i.e., close to the group in Formula I, will be selected to impart to that region of the molecule the molecular structure needed to form a substrate for the enzyme that the compound is intended to be used for. Substituents that are part of the optically detectable label (the $R^1$ group in the various numbered formulas below) will be selected either to enhance the optical or signal detection properties of the label, to impart a particular character to the label that is beneficial for one reason or another, or to avoid interfering with the ability of the label to form a detectable signal. Possible or preferred substituents on any particular group will therefore vary to some degree with the group itself, the location of the group, or the result to be achieved, and in all cases, these substituents will be readily apparent to those skilled in the art. Examples of such substituents are hydroxy, halo (preferably chloro, bromo, or fluoro, and most preferably chloro), nitro, amino, alkylamino (in which the alkyl portion is as defined above, and is preferably lower alkyl, straight-chain and unsaturated), dialkylamino (in which the alkyl portion is as defined above, and is preferably lower alkyl, straight-chain and unsaturated). alkyl (as defined above, and preferably lower alkyl, straight-chain and unsaturated), alkoxy (also as defined above, the alkyl portion of which is preferably lower alkyl, straight-chain and unsaturated), phenyl, and benzyl. Hydroxy, halo, and alkyl substituents are preferred.

The term "residue" when used in reference to an aldehyde denotes the portion of the aldehyde that remains when the —CH=O group has been removed. The term "residue" is also used in reference to a ketone whose ability to be detected by optical means is attributable at least in part to one of the two groups bonded to the carbonyl carbon. The other group bonded to the carbonyl carbon is either $C_1$-$C_2$ alkyl, benzyl, or substituted benzyl. The term "residue" in this case denotes the former group rather than the latter, i.e., the portion of the ketone that remains when the C=O group and the latter group (the $C_1$-$C_2$ alkyl, benzyl, or substituted benzyl) are both removed.

The term "residue of the acid moiety of a pyrethroid" as used herein refers to a segment of a molecule that displays insecticidal activity and that is a member of the class of compounds known as pyrethroids due to their structural similarity to naturally occurring pyrethrins. Pyretliroids generally have a central ester linkage joining a phenoxybenzyl group, which is in some cases substituted, to an organic acid, the phenoxybenzyl group forming the alcohol portion of the ester. The "residue of the acid moiety of a pyrethroid" is the organic acid portion with the —C(=O)—OH removed. In most cases, but not all, the acid is a (2',2'-disubstituted-vinyl)-2,2-dimethylcyclopropanecarboxylic acid, and the residue is a (2',2'-disubstituted-vinyl)-2,2-dimethylcyclopropyl group, as represented by the formula in which $R^{11}$ and $R^{12}$ are any of the substituents described above, and the asterisk denotes the site of the carbonyl group of the ester linkage. Preferred residues are those in which $R^{11}$ and $R^{12}$ are independently alkyl or halo, particularly methyl, chloro or bromo.

The term "carbohydrate residue" is used herein to refer to monosaccharides, oligosaccharides, and polysaccharides in which a hydroxyl group has been removed and serves as the site of bonding to the remainder of the molecule. In preferred embodiments the hydroxyl group that is removed is that located at the site where a typical glycosidic bond is formed (i.e., the position commonly referred to by those skilled in carbohydrate chemistry as the 1-position). Carbohydrate residues thus include, for example, residues of monosaccharides such as glucose, galactose, mannose, rhamnose, fructose, xylose, and ribose, as well as residues of disaccharides such as sucrose, maltose, isomaltose, trehalose, cellobiose, and lactose, and residues of trisaccharides such as maltotriose. The term "substituted carbohydrate residues" refers to monosaccharides, oligosaccharides, and polysaccharides in which one or more of the hydroxyl groups has been replaced with a common substituent such as a carboxylic acid group (—COOH), an amino group (—NH$_2$), a sulfate group (—OSO$_3^-$), or the like. Substituted carbohydrate residues in which the substituent is a carboxylic acid group are of particular interest. One example is a residue of glucuronic acid.

The term "fatty acid residue" is used herein to refer to fatty acids in which the —COOH group has been removed. The residue is generally a linear or branched hydrocarbyl group, saturated or unsaturated, containing from 3 to 50 carbon atoms, and preferably from 6 to 30 carbon atoms. Examples are the residues of butyric, lauric, palmitic, stearic, linoleic, linolenic, arachidonic, oleic, and palmitoleic acids.

The term "optical detection" is used herein to refer to detection by either the emission or absorption of light or electromagnetic energy, either in the visible range or otherwise. Detection by UV absorption, colorimetry, and fluorescence emission are preferred methods of detection. UV absorption is detectable by conventional UV spectrophotometry. UV absorption is particularly useful for substrates of the invention that produce aldehydes that are conjugated to another unsaturated system such as an aryl (particularly naphthyl) group or a heteroaryl group, since these aldehydes have a very strong UV absorbance and red shift. Colorimetry is useful for certain aldehydes produced by this invention, permitting detection in the visible region of a calorimeter or histochemical detection. Colored aldehydes are particularly useful in monitoring enzymes that are localized in media lacking pigments or in situ in plants. Detection can be achieved into the near IR or IR region of the spectrum.

Fluorescence detection can be performed on a fluorimeter, a microplate reader, microdroplets, or in situ. These methods can also be used for detection by fluorescence resonance energy transfer or fluorescence quench. Fluorescence can be measured directly or in a time-resolved manner.

Enzyme Substrates

The enzyme substrates of this invention are cyanohydrin esters and ethers having the generic formula (I)

in which the structure of the $R^3$ group determines whether the compounds are esters or ethers. Compounds of Formula I serve as substrates for enzymes whose enzymatic activity results in replacement of the —O—$R^3$ group with an —OH group, thereby converting these esters and ethers to cyanohydrins of the formula (II)

This conversion may occur either as the result of a cleavage of the bond between the O atom and the $R^3$ group or through conversion of the —O—$R^3$ group to an intermediate which then rearranges and dissociates to form the —OH group. An example of a cleavage to achieve the cyanohydrin is the action of an esterase on a substrate in which $R^3$ is an acyl group. Another example is the action of a phosphatase on a substrate in which $R^3$ combined with the O atom shown in the formula is a phosphate group. A third example is the action of a sulfatase on a substrate in which $R^3$ combined with the O atom shown in the formula is a sulfate group.

An example of a conversion through an intermediate followed by rearrangement or dissociation to achieve the cyanohydrin is the action of a cytochrome $P_{450}$ on a substrate in which $R^3$ is an alkyl or substituted alkyl group, the enzyme hydroxylating the alkyl group to form a hemiacetal intermediate which decomposes in acidic media to a hydroxyl group, thus forming the cyanohydrin.

A second example of a conversion through an intermediate is the action of an epoxide hydrolase on a substrate in which $R^3$ is in which $R^4$ is an oxiranyl alkyl, oxiranyl alkoxy, oxiranylamino, or any of these groups substituted. The action of the epoxide hydrolase converts the substrate to a diol as an intermediate, which then cyclizes spontaneously to release a cyclic ester, carbonate or carbamate leaving a cyanohydrin of Formula II.

A third example of a conversion through an intermediate is the action of a glutathione S-transferase on a substrate in which $R^3$ is in which $R^4$ is again an oxiranyl alkyl, oxiranyl alkoxy, oxiranylamino, or any of these groups substituted. The action of the glutathione S-transferase converts the substrate to a conjugate of the enzyme and the substrate while opening the epoxide ring to form an α-hydroxy group. The intermediate cyclizes spontaneously to release a cyclic ester, carbonate or carbamate coupled to the enzyme, leaving a cyanohydrin of Formula II.

The cyanohydrins of Formula II are proaldehydes or proketones, which in neutral or basic media spontaneously convert to aldehydes or ketones of the formula (III)

In Formulas I, II and III, $R^1$ is the residue of an aldehyde or ketone whose ability to be detected optically by fluorescence emission or light absorptivity is measurably greater than the optical detectability of the cyanohydrin precursor (Formula II) of the aldehyde or ketone or that of the unconverted substrate. The $R^1$ group is a residue of an aldehyde when $R^2$ is H, and a residue of a ketone when $R^2$ is other than H. By "measurably greater" is meant that the aldehyde or ketone (Formula III) can be distinguished from the cyanohydrin (Formula II) or the substrate (Formula I) by conventional means of optical detection, including optical instrumentation, imaging methods, or visual observation by the skilled clinician, the distinction being one that is either quantitative or qualitative.

$R^2$ is either H or a group that will render Formula III a ketone. Of the ketone-type cyanohydrins, those that are most readily synthesized are those in which $R^2$ is either highly reactive or offer at most minimal steric hindrance. $R^2$ groups that meet this description include alkyl groups, preferably lower straight-chain alkyl groups such as methyl and ethyl, that are substituted with an aromatic group at an α-position relative to the ketone. Benzyl and substituted benzyl (with the substituents described above) are examples of these groups. Examples of $R^2$ groups that offer little or minimal steric hindrance are lower straight-chain alkyl groups such as methyl and ethyl. Other groups of both types (i.e., highly reactive or sterically unhindered) will be readily apparent to the skilled synthesis chemist.

The identity of $R^3$ is determined by the purpose that the resulting overall molecular structure (Formula I) is designed to serve. Since a preferred use of these structures is as enzyme substrates in assays or other procedures detecting the presence, absence, or activity level of particular enzymes, $R^3$ will be selected to render the compound of Formula I an effective substrate for the enzyme, i.e., and in many cases one with which the enzyme of interest will specifically and selectively interact to cause replacement of the —O—$R^3$ group of the substrate with an —OH group, thereby producing the proaldehyde or proketone (Formula II). Thus, for example, to provide substrates for esterases, $R^3$ will be an acyl group of appropriate structure to conform to the binding site of the particular esterase sought to be detected; to provide a substrate for β-glucuronidase, $R^3$ will be a residue of glucuronic acid: to provide a substrate for alkaline phosphatase, $R^3$ will be the $PO_3^-$ group; to provide a substrate for a sulfatase, $R^3$ will be the $SO_2^-$ group; to provide a substrate for a protease. $R^3$ will be an amino group bonded to the peptide chain upon which the particular protease will act; and to provide substrates for cytochrome $P_{450}$ proteins, $R^3$ will be an alkyl or other hydrocarbon group that will serve as an effective substrate for the $P_{450}$ protein of interest.

In certain cases, such as for example those in which the enzyme of interest is a cytochrome $P_{450}$, the selectivity of the enzyme will also be affected by the structure of the $R^1$ group. For example, when the enzyme is a $P_{450}$ that hydroxylates a particular class of fatty acids, the appropriate $R^1$ will have the structure of a fatty acid within the class or a mimic of such an acid. Accordingly, the choice of the $R^3$ group will be influenced by the activity of the enzyme of interest in the assay, whereas the choice of either the $R^1$ group, the $R^3$ group, or both can influence the specificity or selectivity of the enzyme.

Although the choice of $R^3$ will in many cases be dictated by the enzyme to which the substrate is directed, certain classes of $R^3$ structures are of particular interest. One such class is that in which $R^3$ is either alkyl, substituted alkyl, aralkyl, substituted aralkyl, or (IV)

in which $R^4$ is either alkyl, substituted alkyl, aralkyl, substituted aralkyl, oxiranylalkyl, substituted oxiranylalkyl, oxiranylalkoxy, substituted oxiranylalkoxy, alkylamino, substituted alkylamino, cycloalkylamino, substituted cycloalkylamino, oxiranylamino, substituted oxiranylamino, alkoxy, substituted alkoxy, and the residue of the acid moiety of a pyrethroid.

$R^1$: Residues of Detectable Aldehydes and Ketones

One segment of the large class of residues that serve as $R^1$ in the compounds and methods of this invention are residues of aldehydes or ketones that form fluorescent or colored species. Examples of fluorescent and colored labels that can be derivatized to serve as the $R^1$ moiety are listed in Table I.

TABLE I

Examples of Fluorescent and Colored Labels Useful as $R^1$ acridine and derivatives
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin
coumarin derivatives:

7-amino-4-methylcoumarin (AMC, Coumarin 120)
7-amino-4-trifluoromethylcouluarin (Coumaran 151)
cyanine dyes
cyanosine
4',6-diaminidino-2-phenylindole (DAPI)
5',5"-dibromopyrogallol-sulfonaphthalein (Bromopyrogallol Red)
diethylenetriamine pentaacetate
4-(4'-dimethylaminophenylazo)benzoic acid (DABCYL)
eosin
erythrosin TABLE I-continued Examples of Fluorescent and Colored Labels Useful as $R^1$ ethidium
fluorescein
fluorescein derivatives:

5-carboxyfluorescein (FAM)
5-(4,6-dichlorotriazin-2-yl)aminofluorescein (DTAF)
2',7'-dimethoxy-4'5'-dichloro-6-carboxyfluorescein (JOE)
fluorescamine
IR144
IR1446
4-methylumbelliferone
ortho cresolphthalein
nitrotyrosine
pararosaniline
Phenol Red
B-phycoerythrin
o-phthaldialdehyde
pyrene
pyrene derivatives:

pyrene butyrate
succinimidyl 1-pyrene butyrate
Reactive Red 4 (Cibacron ™ Brilliant Red 3B-A)
rhodamine and derivatives:

6-carboxy-X-rhodamine (ROX)
6-carboxyrhodamine (R6G)
rhodamine B
rhodamine 123
N,N,N',N'-tetramethyl-6-carboxyrhodamine (TAMRA)
tetramethyl rhodamine
riboflavin
rosolic acid
lanthanide chelate derivatives A subclass of $R^1$ groups of interest that form colored, UV-absorbing and fluorescent aldehydes (or ketones) of interest are naphthyl, substituted naphthyl, anthryl, substituted anthryl, phenanthryl, substituted phenanthryl, phenalenyl, substituted phenalenyl, quinolinyl, substituted quinolinyl, N-alkyl quinolinium, substituted N-alkyl quinolinium, acridinyl, substituted acridinyl, N-alkyl acridinium, substituted, n-alkyl acridinium, coumarinyl, substituted coumarinyl, furanocoumarinyl, substituted furanocoumarinyl, fluorenyl, substituted fluorenyl, fluorenonyl, substituted fluorenonyl, acetaminophenyl, indolyl, substituted indolyl, trans-retinyl, resorufinyl, substituted resorufinyl, polymethenyl, and substituted polymethenyl. Here as well, the substitutions are those described above. Using the aldehyde forms for illustration, examples of these species are coumarin carboxyaldehyde furanocoumarin carboxyaldehyde quinoline carboxyaldehyde benzaldehyde naphthaldehyde 6-methoxy-2-naphthaldehyde 6-diethylamino-2-naphthaldehyde anthracene carbaldehyde 9-acridine carboxyaldehyde

2-methyl-9-acridine carboxaldehyde

N-methyl quinolinium aldehyde 9-fluorophenone-2-carboxaldehyde acetaminobenzaldehyde -continued indole-3-carboxaldehyde indole-4-chloro-5-bromo-3-carboxaldehyde trans-retinal phenalene carboxaldehyde resorufin carboxaldehyde Assay Procedures Assays in accordance with this invention, i.e., methods for detecting, monitoring, or measuring the level of enzyme activity of particular enzymes by the use of the cyanohydrin esters or ethers disclosed herein, can be performed using the same general procedures as those of enzyme assays of the prior art. The cyanohydrin produced by the enzyme reaction is converted to the corresponding aldehyde or ketone by exposure to a neutral or basic medium. If the enzymatic reaction is performed in a liquid medium or on a solid support in contact with a liquid medium, the neutral or basic condition is readily achieved by the incorporation of an appropriate buffer in the liquid medium. Buffers of the appropriate pH are widely known and used, and available from suppliers to the chemiccal industry, and the many choices will be readily apparent to those skilled in synthetic and analytical chemistry. Alternatively, an appropriate buffer can be added at the final satge of the assay to adjust the medium to the appropriate pH, particularly when the conversion is the last of a sequence of reactions and earlier reactions in the sequence are best performed at an acidic pH.

Assays in accordance with this invention can be used to detect or measure the level of enzyme activity in order to evaluate enzymes, enzyme inhibitors, enzyme cofactors, or any candidate species or analyte that affects enzyme activity. Multiple assays can be performed simultaneously, using multiwell reaction plates such as Microtiter plates, or using two-dimensional arrays of test materials such as those used in combinatorial chemistry. One or more of the assay reagents or analytes can be immobilized on a solid phase to facilitate the performance of the assay and the differentiation among different assays performed simultaneously.

Detection of the aldehyde or ketone formed as a result of the assay can be achieved by conventional means of optical detection depending on the nature of the $R^1$ group in the enzyme substrate of Formula I. Distinguishing the aldehyde or ketone from other components in the reaction mixture, and particularly from unconverted reporter is achieved in preferred embodiments by wavelength differentiation or other means that reflect the characteristics of the particular aldehyde or ketone. For assays in which detection is achieved by absorption of UV light or light of other wavelength range, the alddehyde or ketone will exhibit a sufficient shift in the absorption maximum to permit a clear differentiation. Similar shifts arise in fluorescent emissions. Once the optical signal is detected, either quantitatively or qualitatively, the signal is correlated with the enzyme activity to serve as an indication of the activity. This can be done by comparing the signal to a standard or a control, and in some cases by the use of a calibrated scale of signal intensity.

The cyanohydrin esters and ethers of this invention can be prepared by conventional chemical synthesis techniques. Conventional reagents for the placement of a cyano group on an alkyl moiety or carbon atom can be used. In many cases, cyanotrimethylsilane is an effective reagent; in others, potassium cyanide or cyanogen bromide can be used. Other reagents and the appropriate conditions under which the synthesis is performed will be readily apparent to those skilled in the art.

One example of a general synthesis route for a cyanohydrin ester of this invention that uses an aldehyde $R^1CHO$ as a starting material (in which $R^1$ is as defined above), is combined with cyanotrimethylsilane over a suitable solvent such as tetrahydrofuran in the presence of a catalyst such as zinc iodide, to form the cyanotrimethylsilyl ether, which is then reduced to form the cyanohydrin. The cyanohydrin is then reacted with an acyl chloride in tetrahydrofuran followed by the addition of pyridine to form the ester. To form a carbamate rather than a simple ester, the cyanohydrin can be reacted with an appropriate isocyanate in tetrahydrofuran followed by the addition of 4-dimethyl aminopyridine.

Cyanohydrin ethers can likewise be prepared from aldehydes by conventional methods. To form simple ethers, such as methyl or ethyl ethers, an aldehyde $R^1CHO$ can be combined with trimethyl orthoformate or triethyl orthformate, for example, in methanol (or ethanol in the case of triethyl orthoformate) with zinc chloride catalyst to form a dimethox (or diethoxy) intermediate, followed by reaction with cyanotrimethylsilane and boron trifluoride etherate, to form the cyanohydrin methyl (or ethyl) ether. More complex ethers can be formed by reacting the aldehyde with an activating agent such as p-toluene sulfonyl chloride and potassium cyanide in tetrahydrofuran, followed by reaction with an appropriate alcohol at elevated temperature.

The carbon atom to which the cyano group is attached, in certain cyanohydrin ethers and esters in accordance with this invention, can be one of four different substituents attached to that carbon atom, which renders these cyanohydrins ethers and esters chiral structures. In cases where chiral substrates are of importance, this permits the synthesis of more selective reporters. Pyrethroids, for example, are commercially available either as totally racemic. partially purified, or optically and geometrically pure materials, with multiple optical centers. It is therefore valuable in such cases to use reporters that are specially designed to achieve the chiral recognition of enzymes.

Chiral cyanohydrin ethers and esters can be prepared by two methods. In the first method, the racemic cyanohydrin is coupled to an optically pure moiety. A reporter for esterase detection, for example, can be made by coupling a racemic cyanohydrin to an optically pure acid. The resulting diastereomers are then separated by chromatography or crystallization. In the second method, the cyanohydrin itself is synthesized in an optically pure form, using reagents and procedures known in the art.

Further descriptions of cyanohydrin syntheses are found in the following references, the contents of each of which are incorporated herein by reference:

Gassman, P. G., and J. J. Talley, "Cyanohydrins—A General Synthesis," Tetrahedron Letters, no. 40, 3773–3776 (1978)

Effenberger, F., "Synthesis and Reactions of Optically Active Cyanohydrins," Angew. Chem. Int. Ed. Engl., vol. 33, 1555–1564 (1994)

Gröger. Harald, Emine Capan, Anita Barthuber, and Klaus-Dieter Vorlop, "Asymmetric Synthesis of an (R)-Cyanohydrin Using Enzymes Entrapped in Lens-Shaped Gels," Org. Lett., vol. 3, no. 13, 1969–1972 (2001)

Corey, E. J., and Zhe Wang, "Enantioselective Conversion of Aldehydes to Cyanohydrins by a Catalytic System With Separate Chiral Binding Sites for Aldehyde and Cyanide Components," Tetrahedron Letters, vol. 34, no. 25, 4001–4004 (1993)

Kanai, Motomu, Yoshitaka Hamashima and Masakatsu Shibasaki, "Design of a New Bifunctional Asymmetric Catalyst From Carbohydrates: Application to Catalytic Asymmetric Cyanosilylation of Aldehydes and Acetophenone." Tetrahedron Letters. vol. 41, 2405–2409 (2000)

Tanaka, Kenzo, Atsunori Mori, and Shohei lnoue. "The Cyclic Dipeptide cyclo[(S)-Phenylalanyl-(S)-HISTIDYL] as a Catalyst for Asymmetric Addition of Hydrogen Cyanide to Aldehydes," J. Org. Chem., vol. 55, 181–185 (1990)

Applications

This invention is generally applicable to the detection of enzyme activity capable of converting an ether or ester to a hydroxy compound by replacement of an —O—R group, where R is other than H, in the ether or ester to —OH. The term "ester" in this context is used herein to include carbon-atom esters, including simple esters, as well as carbonates and carbamates, plus non-carbon atom esters such as phosphate esters and sulfate esters. The appropriate reporter compound will be a corresponding ether or ester with a —CN group at the appropriate location to form the cyanohydrin upon enzymatic action. This section sets forth a non-limiting set of enzymes whose activity can be detected by the practice of this invention.

Cytochromes $P_{450}$

The cytochrome $P_{450}$ superfamily is a highly diversified set of heme-containing proteins that are widely distributed in animal and plant tissues and in microorganisms, and serve a wide variety of biological functions. Among these functions are the metabolism of drugs by the oxidation of functional groups on the drug molecules, as well as the degradation of toxins. In many cases, drugs are administered to either induce or inhibit the action of a particular $P_{450}$. Screening tests are often performed for novel compounds that will serve as inhibitors of particular $P_{450}$'s to guard against drug-drug interaction.

Examples of reporter molecules for general $P_{450}$'s are as follows:

Certain $P_{450}$'s are used for regulating blood pressure by hydroxylating the terminal position of fatty acids. For the latter $P_{450}$'s, a suitable reporter molecule is one with a fatty acid mimic as $R^1$ of Formula I and a methoxy group as $R^3$ (and preferably hydrogen atom as $R^2$), the fatty acid mimic group further containing a moiety that will provide the final aldehyde or ketone with the desired optical detection character. Examples of such reporter molecules are as follows:

As noted above, the action of a $P_{450}$ on these reporter molecules is to hydroxilate the methyl group to form a hydroxymethyl, group and thus a hemiacetal which decomposes in acidic media to formaldehyde and the cyanohydrin.

Epoxide Hydrolases

Mammalian and insect xenobiotic metabolizing microsomal epoxide hydrolases metabolize drugs and toxins. Many epoxides are potent toxins and carcinogens and epoxide hydrolases are thus important in controlling these substances. Certain biologically useful lipid epoxides, on the other hand, are hydrated (and thereby rendered ineffective) by mammalian soluble epoxide hydrolases, and pharmaceuticals are often sought that will inhibit these hydrolases. Whether their activity is desirable or undesirable, epoxide hydrolases can be detected by appropriate cyanohydrin esters or ethers of the present invention. The action of the epoxide hydrolase on a cyanohydrin ester reporter molecule within the scope of this invention is a ring-forming reaction followed by a ring opening to yield the cyanohydrin. Examples of these reporters, in the form of a simple ester, a carbonate and a carbamate, are as follows:

A further example is as follows:

A still further example, one for the detection of juvenile hormone epoxide hydrolase, is as follows:

While the latter two examples are simple esters, the corresponding carbonates and carbamates have structures analogous to those shown in the three examples immediately preceding.

Glutathione S-Transferases

Glutathione S-transferases reside in both mammals, plants and insects where they, are important in drug and pesticide metabolism. They also metabolize many natural products and are important in the biosynthesis of certain chemical mediators such as leukitriene $D_4$. Glutathione S-transferases that degrade epoxides can be monitored by reporter molecules the same as those used in monitoring epoxide hydrolases, provided that the oxiranyl ring contains an unsubstituted C atom. An examples of such a reporters in the form of a simple ester is as follows:

Esterases

Esterases are important in a variety of biological and physiological functions, one of which is the metabolism of pyrethroids. Rapid, sensitive and selective assays are valuable for enzyme characterization, biological and physiological studies, and pyrethroid exposure monitoring. Unfortunately, research in pyrethroid hydrolases is hampered by the non-specificity of common esterases. In addition, crude enzyme preparations cotain a large number of esterases that are capable of hydrolyzing many reporter substrates. This makes it difficult to accurately assess the ability of a particular enzyme to hydrolize a pyrethroid selectively. In accordance with the present invention, the residue of a the acid moiety of a pyrethroid can be used as a moiety in the substrate of the invention to form a reporter with a high degree of selectivity. The reporter can then be used in screening for enzymes that are capable of bioremediation of pyrethroid insecticides. An example of a reporter in accordance with this invention that has specificity for pyrethroid esterases is as follows:

Lipases

Lipases catalyze the hydrolysis of fats to glycerols and fatty acids. Certain lipases, such as phospholipase A2, are drug targets, others are industrial enzymes, still others are used in home detergents, and still others are targets for fungicide action. An example of a reporter molecule for lipase activity is as follows:

Proteases

Proteases are detected and monitored for a variety of clnical and research purposes. Examples are leucine aminopeptidase, casepsin B, penicillin G acylase, and angiotensin converting enzyme. An example of a reporter molecule for penicillin G acylase activity is as follows:

β-Glucuronidase

Glucuronides are common mammalian metabolites of foreign compounds and are frequently analyzed in toxicology and pharmaceutical chemical studies. β-Glucuronidase (GUS) is commonly used as a reporter for glucuronides, and assays for glucuronides therefore often involve the detection of β-glucuronidase activity. β-Glucuronidase is also used for monitoring transfection, for assessing promoter activity, and for testing plants to detect the presence of transgenes. Examples of reporter molecules for β-glucuronidase activity are as follows:

Enzymes Active on Carbohydrates and Related Substrates

Cellulases, pectinases, galactosidases and similar enzymes are frequently monitored and detected for a variety of reasons. Examples of cyanohydrin ether reporter molecules for galactosidase activity are as follows:

Alkaline Phosphatase

Alkaline phosphatase is a common reporter enzyme for ELISA and Western blot procedures. Appropriate reporter molecules of the present invention for the detection of alkaline phosphatase activity are phoshate esters of cyanohydrins. Examples of three such reporter molecules are shown below, the first forming a ketone and the second and third forming aldehydes:

Organisms and Enzymes That Degrade Carbamates and Organophosphates

Insecticidal carbamates and organophosphates are potentially dangerous environmental contaminants, and organisms and enzymes that degrade these compounds are one means of reducing the environmental contamination. Carbamate degradation is also an important part of the therapeutic use of certain drugs that bear free amino groups. These drugs are administered in carbamate form as prodrugs, the carbamate form being more stable and biologically inactive. An example of a carbamate prodrug is irinotecan, also known as CPT-11, which is used as a treatment for colon and colorectal cancer. Other carbamate antineoplastic prodrugs are paclitaxel and camptothecin.

Continuing research is thus directed toward finding organisms and enzymes that degrade either carbamates or organophosphates for environmental purposes, and carbamate prodrugs for improved therapeutic purposes. These searches are made easier and more sensitive by the use of reporters of the present invention. The two phosphate cyanohydrin esters shown above are examples of reporters that can be used for screening organophosphate degradation candidates. The carbamate ester shown below is an example of a reporter that can be used to screen for carbamate degradation candidates:

in which R denotes the remainder of the insecticidal carbamate molecule or the carbamate prodrug molecule or a mimic of that portion of the molecule. The group R may thus for example be alkyl, aryl, aralkyl, cycloalkyl, or substituted versions of these groups. One specific example of a carbamate ester substrate within this description is:

The following examples are offered for purposes of illustration and are not intended to limit the scope of the invention.

SYNTHESIS EXAMPLES

Esterase Substrates

Example 1

(R/S)-Acetic Acid Cyano-(6-methoxy-naphthalen-2-yl) Methyl Ester

Synthesis of ((R/S)-hydroxy-(6-methoxy-naphthalen-2-yl)-acetonitrile. Zinc iodide (50 mg) was added to a solution of methoxynaphthaldehyde (1.86 g, 10 mmol) in 4.5 mL of $CHCl_3$ and stirred under $N_2$ with cooling in ice bath. Then one half of 11 mmol cyanotrimethylsilane was injected at ambient temperature and the solution was allowed to cool slowly to ~30° C. The remainder of the cyanotrimethylsilane was injected after a few minutes, and the mixture was warmed to 40° C. for 10 minutes, and then stirred for 1.5 hours to at ambient temperature. The reaction mixture was stirred with a mix of 15 mL of glyme (ethylene glycol dimethyl ether) containing 3.5 mL of 3 N HCl under fume hood (excess HCN generated). The process was mildly exothermic. The mixture was then stirred at ambient temperature for 30 minutes, diluted with water and extracted with $CHCl_3$ twice The organic phase was then washed with water and filtered through anhydrous $Na_2SO_4$ to remove any suspended water. The solvent was then stripped to yield 1.91 g (91%) R/S-hydroxy-(6-methoxy-naphthalen-2-yl)-acetonitrile. TLC (thin-layer chromatography) $R_f$ 0.66 (hexane EtOAc=4:1). $^1H$ NMR ($CDCl_3$): δ 2.10 (d, 1H, COH), 3.76 (d, 3H, $CH_3O$), 5.60 (d, 1H, CHCN), 7.02–7.75 (m, 6H, Ar). $M^+$=214.

Synthesis of the title compound. The cyanohydrin formed according to the preceding paragraph (1.06 g, 5 mmol) was dissolved in 7.5 mL of $CHCl_3$ and stirred with ice cooling as 1 mL of acetyl chloride was added rapidly, followed immediately by 1.0 mL of pyridine. After 0.5–1 hour, the mixture was washed twice with water, dried and stripped to give a white solid that was flash chromatographed on silica gel (20 g) column (20% EtOAc in hexane) to recover after vacuum stripping 0.62 g (47%) of (R/S)-acetic acid cyano-(6-methoxy-naphthalen-2-yl) methyl ester, m.p.: 84–85° C. TLC $R_f$ 0.75 (hexane:EtOAc=4:1). $^1H$ NMR ($CDCl_3$): δ 2.20 (d, 3H, $COCH_3$), 3.96 (d, 3H, $CH_3O$), 6.56 (d, 1H, CHCN), 7.16–7.95 (m, 6H, Ar). $M^+$=256.

Example 2

(R/S)-Acetic Acid Cyano-(naphthalen-2-yl) Methyl Ester

This compound was prepared by the procedure of Example 1, with appropriate substitutions in the starting materials. The product was a white cream solid, m.p. 37–38° C. TLC $R_f$ 0.70 (Hexane:EtOAc=3.5:1, v/v). $^1H$ NMR ($CDCl_3$): δ 2.2 (s, 3H), 6.6 (s, 1H), 7.54–7.62 (m, 3H), 7.85–8.04 (m, 4H); $^{13}C$ NMR ($CDCl_3$): δ 20.8 ($CH_3$), 6.34 (CCN), 116.4 (CN), 124.4, 127.2, 127.6, 128.0, 128.2, 128.5, 129.0, 129.6, 132.9, 133.8, 169.0 (C=O); GC/MS: 225 [$M^+$], 183, 165.

Example 3

(R/S)-Butyric Acid Cyano-(naphthalen-2-yl) Methyl Ester

This compound was likewise prepared by the procedure of Example 1, with appropriate substitutions in the starting materials. The product was an oil, TLC $R_f$ 0.82 (Hexane:EtOAc=3.5:1, v/v). $^1H$ NMR ($CDCl_3$): δ 0.96 (t, J=7.2 Hz, 3H), 1.60–1.75 (m, 2H), 2.40 (t, J=7.2 Hz, 2H), 6.61 (s, 1H), 7.46–7.60 (m, 3H), 7.82–8.04 (m, 4H); GC/MS: 253 [$M^+$], 183, 166.

Example 4

Vinylacetic Acid Cyano-(naphthalen-2-yl) Methyl Ester

This compound was likewise prepared by the procedure of Example 1, with appropriate substitutions in the starting materials. The product was an oil, TLC $R_f$ 0.74 (Hiexane:EtOAc=3.5 :1, v/v). $^1$H NMR (CDCl$_3$): δ 3.22 (d, J=6.82 Hz, 2H), 5.20 (d. J=8.37 Hz, 1H), 5.25 (d, J=0.14 Hz, 1H), 5.94 (m, 1H), 6.61 (s, 1H), 7.44–7.62 (m, 3H), 7.80–8.04 (m, 4H); GC/MS: 251 [M$^+$], 183, 166.

Example 5

4-Phenyl-3-butenoic Acid Cyano-(naphthalen-2-yl) Methyl Ester

This compound was likewise prepared by the procedure of Example 1, with appropriate substitutions in the starting materials. The product was a pale brown solid, m.p. 74–75° C. TLC $R_f$ 0.87 (Hexane:EtOAc=3.5:1,/V). $^1$H NMR (CDCl$_3$): δ 3.36 (d, J=1.94 Hz, 2H), 6.28 (s, 1H), 6.52 (m, 1H), 6.63 (d, J=15.48 Hz, 1H), 7.10–7.48 (m, 5H), 7.48–7.70 (m, 3H), 7.76–8.10 (m, 4H); $^{13}$C NMR (CDCl$_3$): δ 38.0 (CH$_2$), 63.6 (CCN), 116.3 (CN), 120.0, 124.4, 124.5, 126.5, 127.3, 127.4. 127.8, 127.9, 128.0, 128.3, 128.6 128.8, 129.7, 133.1, 134.1, 169.0 (C=O); GC/MS: 327 [M$^+$].

Example 6

(trans/cis)-3-(2,2-Dichlorovinyl)-2,2-dimethylcyclopropanecarboxylic Acid Cyano-(6-methoxynaphthalen-2-yl) Methyl Ester (±)-trans/cis-2-(2,2-Dichloroethenyl)-3,3-dimethylcyclopropanecarboxylic acid (0.75 g, 3.59 mmol) in chloroform (1 mL) containing 1 μL of dimethylformamide was treated with thionyl chloride (0.52 mL, 7.12 mmol) and stirred under N$_2$ in an oil bath at 65° C. for 2 hours. The mixture was stripped briefly of solvents, hexane (2 mL) was added and the mixture was stripped again. The residue was dissolved in chloroform (3 mL) and added all at once to an ice-cooled solution of hydroxy-(6-methoxy-naphthalen-2-yl)-acetonitrile (0.64 g, 3 mmol), prepared as described in Example 1, in chloroform (3 mL) and pyridine (0.348 mL), and allowed to stand at ambient temperature for 3 hours. The reaction mixture was washed in order with water, 1 N HCl solution, saturated NaHCO$_3$ solution, water, and dried over Na$_2$SO$_4$. Stripping of solvent gave a pale yellow oil that was flash chromatographed on silica gel (10% ethyl acetate in hexane) yielding 0.72 g (60%) of the title compound. TLC $R_f$ 0.82 (hexane:EtOAc=4:1). $^1$H NMR (CDCl$_3$): δ 1.12 (m, 1H, COCH—), 1.20–1.36 (q, 6H, 2CH$_3$), 1.60 (m, 1H, CHCH=CCl$_2$), 4.14 (d, 3H, OCH$_3$), 5.56 (q, 1H, CHCH=CCl$_2$), 6.56 (d, 1H, CHCN), 7.15–7.94 (m, 6H, Ar). M$^+$=404.

Example 7

(trans/cis)-3-(2,2-Dichlorovinyl)-2,2-dimethylcyclopropanecarboxylic Acid Cyano-(naphthalen-2-yl) Methyl Ester

This compound was prepared by following the procedures of Example 6, with appropriate substitutions in the starting materials. The trans- and cis- products were prepared individually. The trans- product was an oil, TLC $R_f$ 0.88 (Hexane:EtOAc=3.5:1, v/l.). $^1$H NMR (CDCl$_3$): δ 1.23–1.35 (6H, 2 CH$_3$), 1.68 (d, J=8.03 Hz, 1H, CH), 2.34 (dd, J=8.03, 7.5 Hz, 1H, CH), 5.62 (d, J=7.5 Hz, 1H, CH=CCl$_2$), 6.6 (s, 1H), 7.50–7.68 (m, 3H), 7.82–8.08 (m, 4H); $^{13}$C NMR (CDCl$_3$): δ 20.5, 22.8, 34.2, 34.9, 35.6, 63.5 (CCN), 116.5 (CN), 124.5, 126.4, 127.3, 127.8, 128.1, 128.2, 128.4, 128.6, 129.6, 130.0, 133.0, 134.0, 169.5 (C=O); GC/MS: 374 [M$^+$]. The cis- product was an oil, TLC $R_f$ 0.88 (Hexane:EtOAc=3.5:1 v/v). $^1$H NMR (CDCl$_3$): δ 1.18–1.40 (6H, 2 CH$_3$), 1.91 (d, J=8.72 Hz, 1H, CH), 2.12 (dd, J=8.72, 4.41 Hz, 1H, CH), 6.22 (d, J=4.41 Hz, 1H, CH=CCl$_2$), 6.53 (s, 1H), 7.52–7.60 (m, 3H), 7.84–8.14 (m, 4H); $^{13}$C NMR (CDCl$_3$): δ 15.2, 28.4, 29.0, 3.14, 33.7, 63.2 (CCN), 119.8 (CN), 124.1, 124.2, 124.3, 124.5, 125.0, 127.3, 127.8, 128.1, 128.2, 128.7, 133.1, 169.0 (C=O); GC/MS: 374 [M$^+$].

SYNTHESIS EXAMPLES $P_{450}$ Substrates

Example 8

Methoxynaphthalene-2-yl Acetonitrile

A mixture of 1.562 g (10 mmol) 2-naphthylaldehyde, 1.74 g (16.4 mmol) fresh distilled trimethyl orthoformate, 4.2 mL absolute methanol and 10 mg zinc chloride was refluxed for 6 hours under dry condition. The solvent was then partly removed and another 0.5 mL trimethyl orthoformate was added. The reaction mixture continued to reflux overnight and was monitored by TLC. Excess trimethyl orthoformate and solvent were removed under reduced pressure, and the residue was added to aqueous sodium bicarbonate and extracted with diethyl ether, washed with water, dried on magnesium sulfate and concentrated. The crude dimethyl acetal was used for the next step without further purification. Under nitrogen, the crude dimethyl acetal and 1.33 mL (0.992 g, 10 mmol) cyanotrimethylsilane were added gradually to 0.1 mL (0.7 mmol) of boron trifluoride diethyl etherate at 0° C. The mixture was stirred at room temperature for 2 hours, during which time the clear solution turned to a cream slurry. TLC indicated that the reaction was complete. The product mixture was worked up with dilute aqueous sodium bicarbonate, filtered, washed with water and dried in vacuo to give 1.62 g crude product of yield 82.4%, which was recrystallized with diethyl ether to give a white creamy solid, m.p. 47–48° C. TLC $R_f$ 0.60 (Hexane:EtOAc=3.5:1, v/v). $^1$H NMR (CDCl$_3$): δ 3.56 (s, 3H), 5.39 (s, 1H), 7.50–7.57 (m, 3H), 7.82–8.00 (m, 4H); $^{13}$C NMR (CDCl$_3$): δ 57.4 (CH$_3$), 72.7 (CCN), 117.2 (CN), 124.3, 127.1, 127.2, 127.4, 128.0, 128.5, 129.4, 130.6, 133.1, 133.9; GC/MS: 197 [M$^+$], 166 [M$^+$—OCH$_3$], 139.

Example 9

Ethoxynaphthalene-2-yl Acetonitrile

Using the procedure of Example 8 except with triethyl orthoformate instead of trimethyl orthoformate and ethanol instead of methanol, the title compound was prepared as a white plate crystal with a yield of 70.62%, m.p. 53–54° C. TLC $R_f$ 0.52 (Hexane:EtOAc=5:1, v/v). $^1$H NMR (CDCl$_3$): δ 1.32 (t, J=6.6 Hz, 3H), 3.65–3.90 (m, 2H), 5.43 (s, 1H), 7.50–7.58 (m, 3H), 7.83–7.98 (m, 4H); $^{13}$C NMR (CDCl$_3$): δ 15.2 (CH$_3$), 66.0 (CH$_2$), 71.1 (CCN), 117.6 (CN), 124.4, 127.0, 127.1, 127.3, 127.9, 128.5, 129.3, 131.1, 133.1, 133.9; GC/MS: 211 [M$^+$], 182 [M$^+$—CH$_2$CH$_3$], 166 [M$^+$—OCH$_2$CH$_3$], 139.

Example 10

Benzyloxynaphthalene-2-yl Acetonitrile

2-Naphthaldehyde (1.562 g, 10 mmol) was dissolved in 2.3 mL tetrahydrofuran, and 1.9 g (10 mmol) of p-toluenesulfonyl chloride was added. Potassium cyanide (0.66 g, 10 mmol) in 2 mL of water was then added dropwise with stirring at a rate sufficient to maintain the temperature below 5° C. in a ice bath. After the mixture was allowed to stand for 1 hour at 0–5° C. with stirring, the solvent was stripped under reduced pressure, and the solid was filtered, washed with ice-cold diethyl ether, dried in vacuo to give 2.52 g of α-cyanonaphthyl toluenesulfonate as a creamy solid. The sulfonate was immediately mixed with 3.5 mL of benzyl alcohol and heated to 80° C. for 2 hours, then filtered and the solution was flash chromatographed on silica gel using (hexane:EtOAc=3.5:1, v/v) as the eluent to give a creamy solid 2.07 g, yield 75.8%, with m.p. 36–37° C. TLC $R_f$ 0.68 (Hexane:EtOAc=5:1, v/v). $^1$H NMR (CDCl$_3$): δ 4.71–4.87 (m, 2H), 5.44 (s, 1H), 7.36–7.44 (m, 5H), 7.54–7.59 (m, 3H), 7.84–8.00 (m, 4H); $^{13}$C NMR (CDCl$_3$): δ 69.9 (CCN), 71.9 (CH$_2$), 117.4 (CN), 124.5, 127.0, 127.3, 127.4, 128.0, 128.5, 128.6 (2 C, phenyl), 128.7, 129.0 (2 C, phenyl), 129.4, 130.8, 133.1, 133.9, 135.9; GC/MS: 273 [M$^+$], 166 [M$^+$—OCH$_2$Ph].

Example 11

Naphthalene-2-yl Pentyloxy Acetonitrile

Using the procedure of Example 10 except with pentyl alcohol instead of benzyl alcohol, the title compound was prepared as a pale yellow oil with a yield of 69.3%. TLC $R^f$ 0.76 (Hexane:EtOAc=3.5:1, v/v). $^1$H NMR (CDCl$_3$): δ 0.88 (t, J=8.5 Hz, 3H), 1.166–1.42 (m, 4H), 1.55–1.74 (m, 2H), 3.40–3.80 (m, 2H), 5.42 (s, 1H), 7.42–7.62 (m, 3H), 7.74–8.00 (m, 4H); $^{13}$C NMR (CDCl$_3$): δ 14.4 (CH$_3$), 22.8, 28.5, 29.3, 70.5, 71.3 (CCN), 117.7 (CN), 124.4, 126.9, 127.0, 127.5, 128.0, 128.1, 128.5, 129.3, 130.0, 133.2; GC/MS: 253 [M$^+$], 167 [M$^+$—OC$_5$H$_{11}$].

SYNTHESIS EXAMPLES

Epoxide Hydrolase Substrates

Example 12

3-Ethyl-oxiranyl)-acetic Acid Cyanonaphthalen-2-yl-methyl Ester

Under a nitrogen atmosphere, 2-naphthaldehyde (1.1 g, 7.043 mmol) was dissolved in 0.8 mL tetrahydrofuran, and half portions of both 1 mL (0.7424 g, 7.483 mmol) cyanotrimethylsilane and 10 mg zinc iodide were added at 0° C. The resulting mixture was stirred for 5 minutes, after which time the remaining portions of the cyanotrimethylsilane and 10 mg zinc iodide were added. The mixture was stirred at room temperature for 2.5 hours. TLC then indicated that all aldehyde had been consumed. The solvent was stripped under reduced pressure. Hydrochloric acid (2.14 mL, 3N HCl) was added and the mixture stirred vigorously at room temperature for 10 minutes. The naphthalene-2-yl cyanohydrin thus formed was filtered, washed with water, dried in vacuo overnight and then dried in an oven (40–45° C.) for 2 hours to give a creamy solid, whose weight was 1.28 g, yield 99.75 %, m.p. 108–109 C. TLC $R_f$ 0.44 (Hexane:EtOAc=3.5:1, v/v). $^1$H NMR (CDCl$_3$): δ 2.80 (s., 1H, OH), 5.67 (s, 1H), 7.54–7.62 (m, 3H), 7.86–8.03 (m, 4H).

trans-3-Hexenoic acid (0.993 g, 8.7 mmol) was mixed with thionyl chloride (2.93 g, 24.65 mmol), dry benzene (1.8 mL), and 2 drops of dry dimethyl formamide. The mixture was heated to 65° C. for 3 hours. Most of the excess thionyl chloride and benzene were then removed under reduced pressure. Another 3 mL of dry benzene was then added and the solvent was again evaporated to yield 1.32 g of the crude acyl chloride as a pale brown oil. The crude acyl chloride was dissolved in 2 mL dry tetrahydrofuran and added to the naphthalene-2-yl cyanohydrin prepared according to the preceding paragraph, in 2 mL dry tetrahydrofuran at 0° C., followed by addition of 0.9 mL dry pyridine. The reaction mixture was stirred at room temperature overnight and the solvent was stripped from the mixture by a rotary evaporator. The resulting residue was added to water, extracted with diethyl ether, and the ether phase was washed with water, dried on magnesium sulfate, concentrated, and flash chromatographed on silica gel using hexane/EtOAc (3.5/1, v/v) as the eluent to yield the hexenoic ester, which was a pale brown oil.

While a solution of the hexenoic ester in 5 mL of dichloromethane was cooled in an ice bath, meta-chloroperbenzoic acid (0.65 g, 2.9 mmol, max. 77 %) was added to the solution, and the reaction mixture stirred at room temperature overnight (15 hours). TLC then indicated that all hexenoic ester had been converted to epoxide. Dilute sodium bicarbonate was then added to pH 7.3–7.7, and the solution was extracted with diethyl ether, washed with water, dried on magnesium sulfate and concentrated to give 1.46 g creamy solid product, total yield 70.3 %. Without further purification, the purity was indicated by GC/MS as >95 %, with m.p. 60–61° C. TLC $R_f$ 0.45 (hexane:EtOAc= 3.5:1, v/v). $^1$H NMR (CDCl$_3$): $\delta$ 0.98 (t, J=4.2 Hz, 3H), 1.56–1.62 (m, 2H), 2.66–2.80 (m, 3H), 3.04–3.12 (m, 1H), 6.64 (s, 1H), 7.54–7.60 (m, 3H), 7.86–8.08 (m, 4H); $^{13}$C NMR (CDCl$_3$): $\delta$ 10.0, 25.0, 37.6, 53.4, 59.9, 63.7, 116.2, 124.4, 127.4, 127.9, 128.0, 128.4, 128.6, 129.7, 130.4, 133.0, 134.0, 168.8; GC/MS: 295 [M$^+$], 183, 166.

Example 13

Cyclohexylcarbamic Acid Cyanonaphthalene-2-ylmethyl Ester

Naphthalen-2-yl-cyanohydrin (0.61 g, 3.33 mmol), as prepared according to Example 12, was dissolved in 1.5 mL dry tetrahydrofuran and stirred while cooled in an ice bath. Cyclohexylisocyanate (0.426 g, 3.33 mmol) in 1.5 mL dry tetrahydrofuran was then added followed by 4-dimethyl aminopyridine (10 mg). The reaction stirred overnight at room temperature and the solvent was stripped by a rotary evaporator under reduced pressure. The residue was mixed with dilute aqueous sodium bicarbonate, and filtered, washed with water, and dried in vacuo to give 0.916 g of a white solid, yield 89.2 %, which was then recrystallized with ethanol to give a white plate crystal, m.p. 142–143° C. TLC $R_f$ 0.88 (hexane:EtOAc=3.5:1, v/v). $^1$H NMR (CDCl$_3$): $\delta$ 1.2 (m, 5H), 1.62 (m, 5H), 3.52 (m, 1H), 7.54–7.60 (m, 3H), 7.84 (m, 4H), 8.2 (s, 1H, NH); $^{13}$C NMR (CDCl$_3$): $\delta$ 24.65 (2 C), 25.3, 33.06 (2 C), 50.46, 63.55 (CCN), 116.4 (CN), 124.0, 126.75, 127.2, 127.5, 127.6, 128.2, 129.0, 132.8, 133.0, 133.5, 152.5 (C=O); GC/MS: 125, 156.

KINETIC STUDIES

Example 14

Rate of Conversion of Cyanohydrin to Aldehyde

This example illustrates the rate of conversion of a cyanohydrin formed in the practice of this invention to its corresponding aldehyde. The cyanohydrin used in this example is hydroxy-(6-methoxynaphthalen-2-yl) acetonitrile, which is the cyanohydrin formed by the action of an esterase on the substrate of Example 1.

Figure 1:
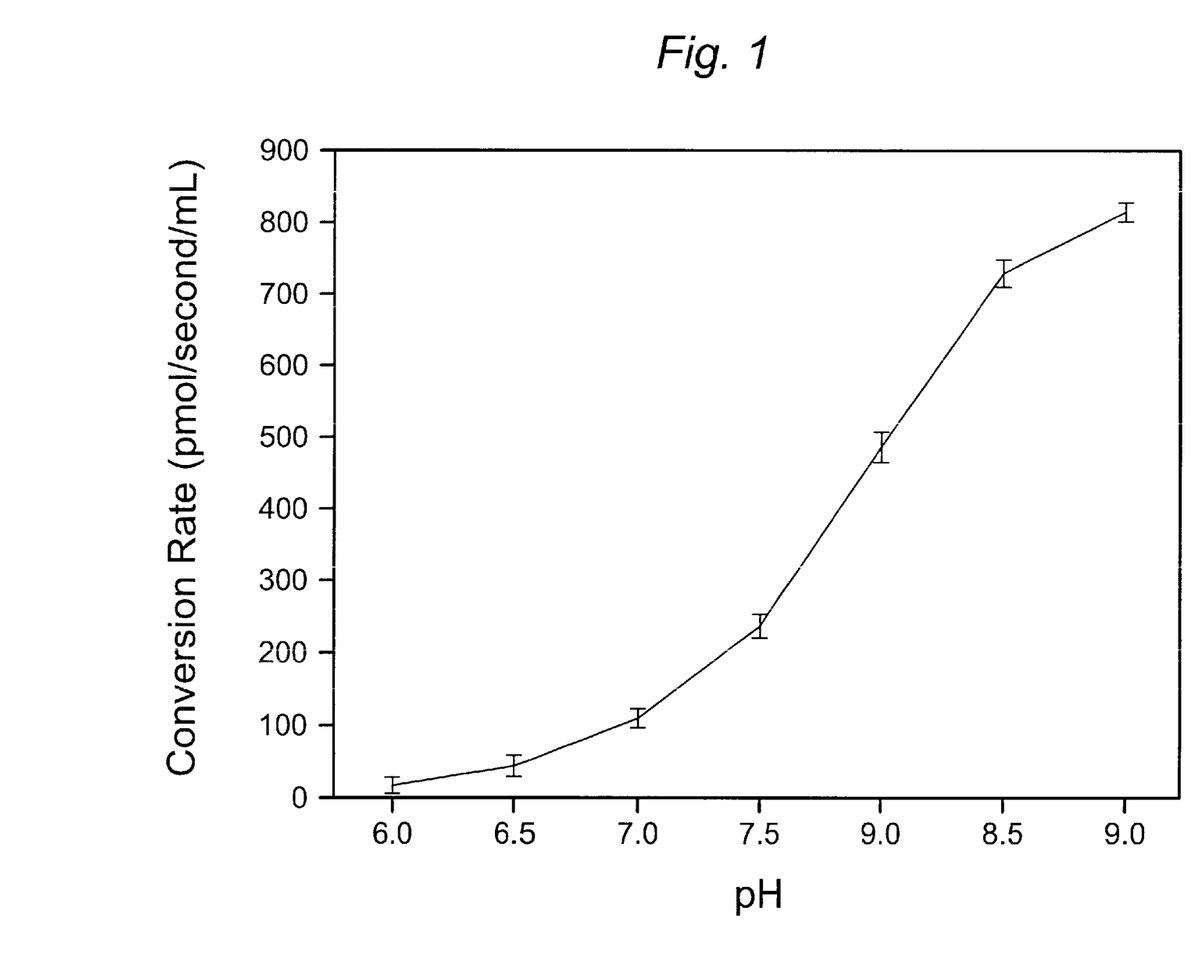
FIG. 1 is a plot of the rate of conversion of cyanohydrin to aldehyde over a range of pH.

The rate of cyanohydrin-to-aldehyde conversion was determined as a function of pH at constant ionic strength (0.1 M) and temperature (25° C.), using a series of tris-maleate buffers with different pH values ranging from 6.0 to 9.0 at intervals of 0.5. Conversion was initiated by the addition of 3 $\mu$L of 10 mM of cyanohydrin, and the formation of 6-methoxy-2-naphthaldehyde, measured in pmol cyanohydrin converted per second per mL, was detected by fluorescence excitation at 330 nm and emission at 460 nm over a time period of 20 minutes. The results are shown in FIG. 1, which indicates that the conversion from cyanohydrin to aldehyde is pH dependent, and that the conversion is promoted by basic conditions. The rate of aldehyde conversion increases rapidly at pH 8.0 or greater with maximum fluorescence achieved in less than 20 seconds.

Example 15

Change in Optical Properties Upon Action of Enzyme: Comparison Between Substrates of Invention and Substrates of Prior Art This example illustrates the degree of change in optical properties, and hence the detectability, of two substrates in accordance with this invention upon action by enzymes, and compares these with the corresponding degree of change for two substrates of the prior art. The substrates representing the invention were (R/S)-acetic acid cyano-(6-methoxynaphthalen-2-yl)-methyl ester (the title compound of Synthesis Example 1 above) and (trans/cis)-3-(2,2-dichlorovinyl)-2,2-dimethylcyclopropanecarboxylic acid cyano-(6-methoxynaphthalen-2-yl)-methyl ester (the title compound of Synthesis Example 2 above). The substrates of the prior art were methylumbelyl acetate (for detection by fluorescence emission) and 2-naphthacetate (for detection by UV absorption) in assay solutions with different pH values. These prior art substrates were selected because both are widely used and both have aromatic systems similar to the two test compounds.

Using tris-maleate at pH levels of 6.5, 7.5, and 8.5, UV studies were performed at concentrations of 10 $\mu$M, and the optical densities and molar absorptivities of the starting esters and the hydrolysis products (naphthol in the case of 2-naphthacetate and 6-methoxy-naphthaldehyde in the case of the Example 1 substrate) were determined by conventional instrumentation. The results are listed in Table II in which "2-NA" denotes 2-naphthacetate, "Compound I" denotes the Example 1 substrate, "OD" denotes optical density, and "$\epsilon$" denotes molar absorptivity.

TABLE II

Change in Optical Properties: Invention vs. Prior Art

| pH | Detection Method | | 2-NA | | Compound I | |
|---|---|---|---|---|---|---|
| | | | ester | naphthol | cyanoester | aldehyde |
| 6.5 | UV | $\lambda_{max}$ (nm) | 284 | 285 | 287 | 314 |
| | UV | OD | 0.14 | 0.105 | 0.086 | 0.473 |
| | UV | $\epsilon$ | 3,500 | 2,600 | 3,000 | 11,870 |
| 7.5 | UV | $\lambda_{max}$ (nm) | 283 | 284 | 287 | 313 |
| | UV | OD | 0.141 | 0.155 | 0.137 | 0.468 |

TABLE II-continued

Change in Optical Properties: Invention vs. Prior Art

| pH | Detection Method | | 2-NA | | Compound I | |
|---|---|---|---|---|---|---|
| | | | ester | naphthol | cyanoester | aldehyde |
| | UV | ε | 3,500 | 3,870 | 3,420 | 11,700 |
| 8.5 | UV | $\lambda_{max}$ (nm) | 283 | 283 | 287 | 314 |
| | UV | OD | 0.133 | 0.170 | 0.142 | 0.465 |
| | UV | ε | 3,300 | 4,250 | 3,550 | 11,630 |

Again using tris-maleate at pH levels of 6.5, 7.5, and 8.5, fluorescence studies were performed at concentrations of 10 μM, and fluorescence of the starting esters and the hydrolysis products (hydroxycoumarin in the case of methylumbelyl acetate and 6-methoxy-naphthaldehyde in the case of the Example 1 substrate) were determined by conventional instrumentation. The results are listed in Table III in which "MUA" denotes methylumbelyl acetate, "Compound I" denotes the Example 1 substrate, "Ex" denotes the optimal excitation wavelength in nm, "$Em_{max}$" denotes the maximal emission wavelength in nm, and "RFU" denotes the relative fluorescence units multiplied by 1,000.

TABLE III

Change in Optical Properties: Invention vs. Prior Art

| | | | MUA | | Compound I | |
|---|---|---|---|---|---|---|
| pH | Detection Method | | ester | HO-coumarin | cyanoester | aldehyde |
| 6.5 | Fluorescence | Ex | 330 | 330 | 360 | 360 |
| | Fluorescence | $Em_{max}$ | 366 | 460 | 410 | 450 |
| | Fluorescence | RFU | 2,672 | 18,830 | 241 | 17,783 |
| 7.5 | Fluorescence | Ex | 330 | 330 | 360 | 360 |
| | Fluorescence | $Em_{max}$ | 366 | 460 | 450 | 485 |
| | Fluorescence | RFU | 1,350 | 19,025 | 581 | 19,250 |
| 8.5 | Fluorescence | Ex | 330 | 330 | 360 | 360 |
| | Fluorescence | $Em_{max}$ | 366 | 460 | 450 | 510 |
| | Fluorescence | RFU | 1,600 | 19,195 | 3,708 | 19,256 |

The UV absorption data in Table II show that at all three pH levels, the aldehyde hydrolysis product of the substrate of Example 1 had a significantly higher UV absorption at long wavelength (314 nm) than the parent substrate while the UV absorption of 2-naphthol did not change significantly relative to 2-naphthaldehyde. The fluorescence emission data in Table III show that at all three pH levels, the hydrolysis products of both substrates exhibited strong light emission and large Stokes' shift. The hydrolysis product of Compound I however showed a larger red shift under all pH conditions tested, which is important for improving the sensitivity of a fluorescence assay. No effects on emission wavelength or fluorescence intensity were observed at any of the three pH levels for the hydrolysis product of Compound I, while a pH dependency of these properties was apparent for the hydrolysis product of the prior art substrate. The maximal emission peak of the prior art hydrolysis product varied from 450 to 510 nm with increasing pH, and the parent compound also showed a pH-dependent emission peak (from 410 to 450 nm). This small red shift will cause a high background from the substrate at the assay wavelength, and thereby lower the assay sensitivity. The cyanoester parent of compound I, by contrast, had only a low emission peak at 366 nm at all pH levels tested, and essentially no emission at the maximal emission peak of its hydrolysis product (460 nm). This indicates an excellent signal/noise ratio over a wide range of pH.

Example 16

Stability of Substrates Relative to Prior Art Substrates

The same two invention substrates and two prior art substrates were tested for stability by both UV detection and fluorescence detection under typical assay conditions.

Tris maleate buffers (0.1 M) at pH ranging from 6.0 to 9.0 in intervals of 1.0 were used, and substrate was added to 10 μM final concentration. The UV samples were read at 309 nm for 2-naphthacetate and at 320 nm for the two test compounds. The fluorescence samples were read with excitation at 360 nm and emission at 460 nm (for pH 6.0), 465 nm (for pH 7.0), 485 nm (pH 8.0), and 510 nm (pH 9.0) for the methylumbelyl acetate, and with excitation at 330 nm and emission at 460 nm for the two test compounds, in all cases, the readings over 5-minute periods. The results are listed in Table IV, where "2-NA" denotes 2-naphthacetate, "MUA" denotes methylumbelyl acetate, "I" denotes the Example 1 substrate, and "II" denotes the Example 4 substrate.

TABLE IV

Substrate Stability Comparisons: Invention vs. Prior Art

| | UV Absorption (mAbs/min) | | | Fluorescence (pmol/min) | | |
|---|---|---|---|---|---|---|
| pH | 2-NA | I | II | MUA | I | II |
| 6 | <0.01 | <0.01 | <0.01 | 14 | <1 | <1 |
| 7 | 0.05 | <0.01 | <0.01 | 20 | 8 | <1 |
| 8 | 0.44 | <0.01 | <0.01 | 108 | 59 | <1 |
| 9 | 0.555 | 0.103 | 0.05 | 830 | 138 | 10 |

The data in Table IV indicate that both substrates of the invention are superior to the two prior art substrates in stability.

Example 17

Sensitivity to Enzyme Strength

This example illustrates the sensitivity of the substrate to the enzyme, and compares a substrate in accordance with the present invention to two prior art substrates. The substrate representing the invention was (R/S)-acetic acid cyano-(6-methoxynaphthalen-2-yl)-methyl ester (the title compound of Synthesis Example 1 above), and the two prior art substrates, as in the preceding examples, were methylumbelyl acetate (for detection by fluorescence emission) and 2-naphthacetate (for detection by UV absorption). The enzyme was porcine esterase.

A tris-maleate buffer at pH 8.0 (0.1 M) was used. The procedure consisted of adding substrate to a test tube containing 3 mL of buffer to a final substrate concentration of 10 μM, then adding porcine esterase at strengths of 0.06, 0.09. 0.12, 0.18, 0.30, 0.60, 0.9 and 1.2 unit, in which 1 unit=1 μmol/min/mL. UV absorption of 2-naphthacetate and the compound of Synthesis Example 1 (referred to as Compound I) were measured at 310 nm and 314 nm. respectively, while fluorescence detection of methylumbelyl acetate and Compound I were measured with excitation at 460 nm for Compound I and 485 nm for methylumbelyl acetate and emission at 330 nm for Compound I and 360 nm for methylumbelyl acetate. The enzyme sensitivities for each substrate and detection method were defined as the minimal amount of enzyme per mL required to produce a signal from the substrate that was at least three times greater than the background noise. The results are listed in Table V.

TABLE V

Substrate Sensitivity Comparisons: Invention vs. Prior Art

| Substrate | Detection Method | Sensitivity |
|---|---|---|
| 2-Naphthacetate | UV | 0.002 |
| Compound I | UV | 0.001 |
| Compound I | Fluorescence | 0.00002 |
| Methylumbelyl acetate | Fluorescence | 0.0005 |

The data in Table V indicate that the substrate of the invention is superior in sensitivity to each of the two prior art substrates.

Example 18

Response to Different Esterases

This example utilizes the two invention substrates used in the preceding examples and shows how they respond to esterases from four different sources. The esterases were porcine esterase purchased from Sigma Chemical Company, St. Louis, Mo., USA, esterase from a rat liver microsomal preparation from 8-week-old Fisher 344 rats, and homogenates of Heliothis virescens from both pyrethroid-susceptible and -resistant strains of tobacco budworm. The substrate in each case was added to a tris-maleate buffer (pH 8.0, 0.1 m) to a final substrate concentration of 10 $\mu$M, followed by the addition of the enzyme preparation. The samples were then immediately read by fluorometer at 460 nm for one minute (excitation at 330 nm). The results are listed in Table VI, where "Compound I" denotes the Example 1 substrate, and "Compound II" denotes the Example 4 substrate.

TABLE VI

Enzyme Activity of Different Esterases Against Substrates of the Invention

| | Specific Activity (pmol/min/mg protein) | |
|---|---|---|
| Enzyme/Source | Compound I | Compound II |
| Porcine esterase | 2,911,000 ± 1,780 | 142,000 ± 520 |
| Rat liver microsome | 39,800 ± 600 | 270 ± 18 |
| H. virescens (susceptible) | 9,700 ± 220 | 150 ± 9 |
| H. virescens (resistant) | 25,100 ± 425 | 840 ± 22 |

Since porcine esterase is a relatively general esterase and therefore displayed high activity against both substrates. Compound II is a pyrethroid-selective substrate and the esterase from the pyrethroid-resistant H. virescens budworm strain displayed higher activity than the esterase from the pyrethroid-susceptible strain. The comparison between these two strains indicates that elevated pyrethroid esterase activity is associated with the resistance in the strain. The difference is less pronounced with the Compound I substrate, which is not pyrethroid-selective. Thus, enzyme assays using general substrates may be less effective in illustrating the real role of esterases in pyrethroid resistance mechanism, and hence Compound II or related pyrethroid mimetic substrates will be very useful in monitoring resistance mechanisms in insects.

Example 19

Cytochrome $P_{450}$ Substrates: Comparison With Prior Art

This example compares four cytochrome $P_{450}$ substrates within the scope of this invention with two cytochrome $P_{450}$ substrates that are outside the scope of this invention. The four invention substrates were methoxynaphthalen-2-yl acetonitrile (whose synthesis is shown in Example 8 above and which is designated below as Compound III), ethoxynaphthalen-2-yl acetonitrile (synthesis shown in Example 9, Compound IV), benzoxynaphthalen-2-yl acetonitrile (synthesis shown in Example 10, Compound V), and pentoxynaphthalen-2-yl acetonitrile (synthesis shown in Example 11, Compound VI). The substrates outside the scope of the invention were ethoxyresorufin (designated below as Compound A) and pentoxyresorufin (designated below as Compound B). The structures of these last two substrates are as follows:

ethoxyresorufin pentoxyresorufin

All substrates were tested against a microsomal enzyme preparation from 8-week-old Fisher err rats, by first combining 890 mL of the preparation with 2 mL of phosphate buffer (pH 7.6, 0.2 M) and incubating the mixture at 37° C. for 5 minutes. The substrate (10 mL) was then added (10 mM final concentration), followed by an appropriate signal generating system (100 mL). The samples were immediately read by fluorometer at 460 nm for 1 minute with excitation at 330 nm. The results in terms of specific activity, both with and without the enzyme system, are shown in Table VII, in which each entry represents an average of three tests.

TABLE VII

Comparative Substrate Response to $P_{450}$ Enzyme Activity

| | Specific Activity (pmol/min/mg protein) | |
|---|---|---|
| Substrate | Without Enzyme System | With Enzyme System |
| Compound I | 35.5 ± 1.7 | 609.6 ± 21 |
| Compound II | 33.4 ± 2.0 | 102.4 ± 7.5 |
| Compound III | 45.9 ± 3.0 | 275.8 ± 20.5 |
| Compound IV | 40.0 ± 1.2 | 292.6 ± 16.2 |
| Compound A | 52.2 ± 1.9 | 89.0 ± 4.6 |
| Compound B | 41.8 ± 2.2 | 62.5 ± 5.2 |

The substrates of the invention (Compounds I through IV) demonstrate a clear and consistent improvement in sensitivity relative to those of the prior art (Compounds A and B).

The foregoing is offered primarily for purposes of illustration. Further variations, implementations, and applications that embody the spirit and underlying concepts of the invention and thereby fall within its scope will be apparent to those skilled in the art.

What is claimed is:

1. A compound having the formula in which:
- $R^1$ is an aldehyde or ketone group that is optically detectable by fluorescence emission, UV light absorptivity or colorimetry;
- $R^2$ is a member selected from the group consisting of H, $C_1$–$C_2$ alkyl, benzyl, and substituted benzyl; and
- $R^3$ is a member selected from the group consisting of alkyl, substituted alkyl, aralkyl, substituted aralkyl, phosphate, sulfate, carbohydrate residues, substituted carbohydrate residues, and in which $R^4$ is a member selected from the group consisting of alkyl, substituted alkyl, aralkyl, substituted aralkyl, oxiranylalkyl, oxiranylalkoxy, substituted oxiranylalkoxy, alkylamino, substituted alkylamino, peptidylamino, cycloalkylamino, substituted cycloalkylamino, oxiranylamino, substituted oxiranylamino, alkoxy, and substituted alkoxy;

$R^1$ being selected such that the optical detectability of is measurably greater than the optical detectability of 2. A compound in accordance with claim 1 in which $R^2$ is H.

3. A compound in accordance with claim 1 in which $R^1$ is a residue of a fluorescent aldehyde.

4. A compound in accordance with claim 1 in which $R^1$ is a residue of a UV light-absorbing aldehyde.

5. A compound in accordance with claim 1 in which $R^1$ is a residue of a colorimetric aldehyde.

6. A compound in accordance with claim 1 in which $R^3$ is a member selected from the group consisting of alkyl, substituted alkyl, aralkyl, and substituted aralkyl.

7. A compound in accordance with claim 6 in which $R^3$ is a member selected from the group consisting of $C_1$–$C_6$ alkyl, substituted $C_1$–$C_6$ alkyl, phenyl-($C_1$–$C_6$ alkyl), and substituted phenyl-($C_1$–$C_6$ alkyl), and $R^2$ is H.

8. A compound in accordance with claim 6 in which $R^3$ is a member selected from the group consisting of $C_1$–$C_6$ alkyl, hydroxy-substituted $C_1$–$C_6$ alkyl, ($C_1$–$C_3$ alkoxy)-substituted $C_1$–$C_6$ alkyl, halo-substituted $C_1$–$C_6$ alkyl, phenyl-($C_1$–$C_6$ alkyl), and hydroxy-substituted phenyl ($C_1$–$C_6$ alkyl), ($C_1$–$C_3$ alkoxy)-substituted phenyl-($C_1$–$C_6$ alkyl), and halo-substituted phenyl-($C_1$–$C_6$ alkyl), and $R^2$ is H.

9. A compound in accordance with claim 1 in which $R^3$ is

10. A compound in accordance with claim 9 in which $R^4$ is a member selected from the group consisting of alkyl and substituted alkyl.

11. A compound in accordance with claim 10 in which $R^4$ is a member selected from the group consisting of $C_1$–$C_{12}$ alkyl, hydroxy-substituted $C_1$–$C_{12}$ alkyl, ($C_1$–$C_3$ alkoxy)-substituted $C_1$–$C_{12}$ alkyl, and halo-substituted $C_1$–$C_{12}$ alkyl, and $R^2$ is H.

12. A compound in accordance with claim 10 in which $R^4$ is a member selected from the group consisting of $C_1$–$C_6$ alkyl, hydroxy-substituted $C_1$–$C_6$ alkyl, ($C_1$–$C_3$ alkoxy)-substituted $C_1$–$C_6$ alkyl, and halo-substituted $C_1$–$C_6$ alkyl, and $R^2$ is H.

13. A compound in accordance with claim 9 in which $R^4$ is a member selected from the group consisting of aralkyl and substituted aralkyl.

14. A compound in accordance with claim 13 in which $R^4$ is a member selected from the group consisting of phenyl-($C_1$–$C_6$ alkyl) and substituted phenyl-($C_1$–$C_6$ alkyl).

15. A compound in accordance with claim 13 in which $R^4$ is a member selected from the group consisting of phenyl-($C_1$–$C_6$ alkyl), hydroxy-substituted phenyl-($C_1$–$C_6$ alkyl), ($C_1$–$C_3$ alkoxy)-substituted phenyl-($C_1$–$C_6$ alkyl), and halo-substituted phenyl-($C_1$–$C_6$ alkyl), and $R^2$ is H.

16. A compound in accordance with claim 13 in which $R^4$ is a member selected from the group consisting of benzyl and phenylethyl.

17. A compound in accordance with claim 9 in which $R^4$ is a member selected from the group consisting of oxiranylalkyl, substituted oxiranylalkyl, oxiranylalkoxy, substituted oxiranylalkoxy, oxiranylamino, and substituted oxiranylamino.

18. A compound in accordance with claim 17 in which $R^4$ is a member selected from the group consisting of oxiranyl-($C_1$–$C_3$ alkyl), $C_1$–$C_3$ alkyl-substituted oxiranyl-($C_1$–$C_3$ alkyl), oxiranyl-($C_1$–$C_3$ alkoxy), $C_1$–$C_3$ alkyl-substituted oxiranyl-($C_1$–$C_3$ alkoxy), oxiranylamnino, and $C_1$–$C_3$ alkyl-substituted oxiranylamino, and $R^2$ is H.

19. A compound in accordance with claim 1 in which $R^1$ is a member selected from the group consisting of naphthyl, substituted naphthyl, anthryl, substituted anthryl, phenanthryl, substituted phenanthryl, phenalenyl, substituted phenalenyl, quinolinyl, substituted quinolinyl, N-alkyl quinolinium, substituted N-alkyl quinolinium, acridinyl, substituted acridinyl, N-alkyl acridinium, substituted N-alkyl acridinium, coumarinyl, substituted coumarinyl, furanocoumarinyl, substituted furanocoumarinyl, fluorenyl, substituted fluorenyl, fluorenonyl, substituted fluorenonyl, acetaminophenyl, indolyl, substituted indolyl, trans-retinyl, resorufinyl, substituted resorufinyl, polymethenyl, and substituted polymethenyl.

20. A compound in accordance with claim 19 in which $R^1$ is a member selected from the group consisting of naphthyl, anthryl, phenanthryl, quinolinyl, coumarinyl, furanocoumarinyl, fluorenyl, fluorenonyl, acetaminophenyl, indolyl, trans-retinyl, resorufinyl, polymethenyl, and substituted analogs of all of the above in which the substituents are members selected from the group consisting of hydroxy, halo, nitro, amino $C_1$–$C_3$ alkylamino, di-($C_1$–$C_3$-alkyl)-amino, and $C_1$–$C_3$ alkoxy.

* * * * *